United States Patent
Kozak et al.

(10) Patent No.: US 8,033,984 B2
(45) Date of Patent: Oct. 11, 2011

(54) THERAPEUTIC DEVICE FOR ERECTILE DYSFUNCTION

(76) Inventors: Andrzej Wladyslaw Kozak, El Cajon, CA (US); Grazyna Hallns Kozak, El Cajon, CA (US)

( * ) Notice: Subject to any disclaimer, the term of this patent is extended or adjusted under 35 U.S.C. 154(b) by 909 days.

(21) Appl. No.: 12/031,704

(22) Filed: Feb. 15, 2008

(65) Prior Publication Data

US 2009/0209807 A1   Aug. 20, 2009

(51) Int. Cl.
*A61F 5/00* (2006.01)
(52) U.S. Cl. .......................................... 600/38; 600/15
(58) Field of Classification Search ............... 600/38–41, 600/9–15
See application file for complete search history.

(56) References Cited

U.S. PATENT DOCUMENTS

| | | | |
|---|---|---|---|
| 4,643,175 A * | 2/1987 | Chapman ........................ | 600/38 |
| 4,960,113 A | 10/1990 | Seeberg-Elverfeldt | |
| 5,244,454 A * | 9/1993 | Coates ............................ | 600/41 |
| 5,728,043 A * | 3/1998 | Yong ............................... | 600/39 |
| 5,855,548 A | 1/1999 | Place | |
| 6,309,344 B1 | 10/2001 | Werner | |
| 6,348,033 B1 * | 2/2002 | Catlett ............................ | 600/15 |
| 6,589,159 B2 | 7/2003 | Paturu | |
| 7,690,220 B2 * | 4/2010 | Okamura .......................... | 63/3 |
| 2006/0111606 A1 * | 5/2006 | Yee ................................ | 600/15 |
| 2006/0142638 A1 * | 6/2006 | Flores ............................. | 600/38 |
| 2008/0119690 A1 * | 5/2008 | Comeau ......................... | 600/39 |
| 2009/0264700 A1 * | 10/2009 | Kuri ............................... | 600/41 |

* cited by examiner

*Primary Examiner* — John Lacyk
(74) *Attorney, Agent, or Firm* — Ash Tankha; Lipton, Weinberger & Husick (57) ABSTRACT

Disclosed herein is a therapeutic device and method for achieving and sustaining erection of a penile organ. The therapeutic device comprises a flexible belt worn by the user for producing an external pressure on one or more regions of the penile organ. The flexible belt comprises a waist section and a loop section. The waist section is worn around waist of the user for adjusting the external pressure by the user. The loop section is worn on the dorsal region of the penile organ for producing the external pressure. A magnetic unit placed inside the loop section produces a magnetic field. The magnetic field increases level of oxygen to augment blood flow in the penile organ. The magnetic field applied and the adjustment of the external pressure enables the user to achieve and sustain the erection of the penile organ.

10 Claims, 7 Drawing Sheets

NON MAGNETIC HEMATITE STONES 501

| PROPERTY | NATURAL RUBBER LATEX TUBING (DIPPED) | NATURAL RUBBER (EXTRUDED) (AMBER) | NATURAL RUBBER (EXTRUDED) (COLOR) | SYNTHETIC RUBBER TUBING |
|---|---|---|---|---|
| SPECIFIC GRAVITY | 0.92 | 0.95 | 0.98 | 1.00 |
| DUROMETER RANGE SHORE A | 40 +/- 5 | 30 +/- 3 | 38 +/- 3 | 48 +/- 5 |
| TENSILE STRENGTH 1,000 PSI | 4000 | 2500 | 3200 | 2000 |
| ELONGATION% | 800 | 700 | 650 | 500 |
| 100% MODULUS (PSI) | 90 | 250-85 | 130 | 175 |

FIGURE 6

THERAPEUTIC DEVICE FOR ERECTILE DYSFUNCTION

BACKGROUND

This invention, in general, relates to external body therapy. More particularly, this invention relates to a therapeutic device for achieving and sustaining erection of a penile organ.

Erectile dysfunction (ED), also known as impotence, is the inability of a human male to achieve or sustain an erection of the penile organ for satisfactory sexual activity. ED may vary in severity. Some men have a total inability to achieve the erection, while some men have an inconsistent ability to achieve the erection or may sustain only brief erections. A variety of treatment options are available for men with ED including drugs administered orally, drugs administered directly into the penile organ, mechanical aids such as constriction rings and vacuum pumps, and surgical implants such as semi-rigid penile prosthesis, inflatable penile prosthesis, etc.

The conventional penile erection aids or treatments may not be suitable for men with ED. The comorbid conditions arising out of ED affect the choice of treatment to be given to men with ED. Moreover, the aforementioned ED aids and treatments may have associated side effects such as headache, indigestion, muscle pain, back pain, nasal congestion, runny or blocked nose, flushing and dizziness, nausea, mild visual disturbances, or changes in blood pressure. Drugs administered directly into the penile organ may cause burning sensations, minor bleeding, priaprism, or fibrosis. Priaprism is a medical condition of experiencing painful erection of the penile organ. Fibrosis is a medical condition where an excess tissue is formed in an organ as a result of regenerative process. The vacuum pumps and constriction rings may cause uncomfortable erections or may impair ejaculation. Furthermore, there is a risk of infection and bruising in using the constriction rings and the vacuum pumps. In semi-rigid penile prosthesis and inflatable penile prosthesis, the sensation of the penile organ may be reduced and may lead to absence of the ejaculation. Further, the existing ED aids and treatments may not be economical.

ED may be caused due to radical prostatectomy. Radical prostatectomy is an operation performed to remove prostate cancer. The probability of contracting ED increases in men after radical prostatectomy. Hence, early penile rehabilitation is required to maintain a healthy penile tissue after radical prostatectomy. Because of the damage to the penile neural pathway after radical prostatectomy, men lose their natural nocturnal erection and eventually may lead to the fibrosis of the penile tissue. Oral ED therapies are provided generally after radical prostatectomy. During the initial period after radical prostatectomy, the oral ED therapies may not be effective since the penile neural pathway may not have regenerated. Early penile rehabilitation increases the blood flow to the penile organ so that the penile tissue is maintained while the neural pathway regenerates, allowing for more effective oral ED therapy. Hence, there is a need for early penile rehabilitation of the penile tissue in the penile organ.

Erection of the penile organ in men is achieved and maintained through an internal mechanism that forces the blood into the penile organ during sexual activity and drains the blood from the penile organ after the sexual activity. Veins in the penile organ carry the blood out of the penile organ, whereas, arteries in the penile organ carry the blood into the penile organ. As men age, penile veins weaken and leak back into the bloodstream. The blood cavities do not expand enough to allow a full erection of the penile organ. In time, all men experience the aforementioned decline of the erection of the penile organ, no matter how healthy or sexually active they are. The pressure produced by the constriction rings squeezes the veins and the arteries, thereby restricting blood flow into and from the penile organ. Hence, there is a need for applying pressure selectively on the penile organ to allow the flow of blood into the penile organ and to restrict the flow of blood from the penile organ. Research studies have demonstrated that magnets enhance the flow of the blood in the arteries that carry blood into the penile organ and assist in maintaining the erection even after ejaculation. Therefore, there is a need for a therapeutic device to enhance the flow of blood in the penile organ using magnets.

There is an unmet need for a device and method to enhance the flow of blood in the penile organ to achieve erection of the penile organ. Further, there is a need to control and adjust the blood flow by applying pressure selectively on the penile organ for sustaining erection of the penile organ. Furthermore, there is a need for early penile rehabilitation of the penile tissue in the penile organ.

SUMMARY OF THE INVENTION

The therapeutic device and method disclosed herein addresses the above stated needs for achieving and sustaining erection of a penile organ. The device and method disclosed herein enhances the flow of blood in the penile organ, controls and adjusts the blood flow by applying pressure selectively to the penile organ, and enables early penile rehabilitation of the penile tissue in the penile organ.

The therapeutic device comprises a flexible belt worn by a user for producing an external pressure on one or more regions of the penile organ. The external pressure allows the flow of blood into the penile organ and restricts the flow of blood from the penile organ. The flexible belt may be an elastic tube or a cord. The flexible belt includes a waist section and a loop section. A buckle clamp connects the ends of the waist section. The waist section comprises multiple rings for adjusting length of the flexible belt. The rings are placed on the ends of the waist section. The user adjusts length of the flexible belt to provide an external pressure on the penile organ.

The loop section worn on the dorsal region of the penile organ produces the external pressure on the penile organ. The external pressure produced on the penile organ restricts blood flow in veins carrying blood out of the penile organ. Further, the external pressure on the penile organ permits the blood flow in arteries carrying blood into the penile organ. The loop section joins the waist section along posterior end of the user. A magnetic unit placed inside the loop section produces a magnetic field. The magnetic field increases level of oxygen to augment the blood flow in the penile organ. The magnetic unit includes one of magnetized neodymium disc magnets, magnetic hematite stones, or a combination thereof. The magnetic unit is placed at the center of the flexible belt. In an embodiment of the therapeutic device disclosed herein, a non magnetic unit may be placed at the center of the flexible belt for users with implanted pacemakers or any other electronic implanted devices. The non magnetic unit includes one or more non magnetic hematite stones.

The magnetic field applied on the penile region and the adjustment of the external pressure enables the user to achieve and sustain the erection of the penile organ. By using the therapeutic device, a user achieves faster and harder erection and sustains the erection even after ejaculation until the external pressure is applied on the penile organ. By using the therapeutic device, a user with premature ejaculation may sustain the erection even after ejaculation. Further, by using the therapeutic device, early penile rehabilitation of the penile tissue in the penile organ is achieved.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1A:
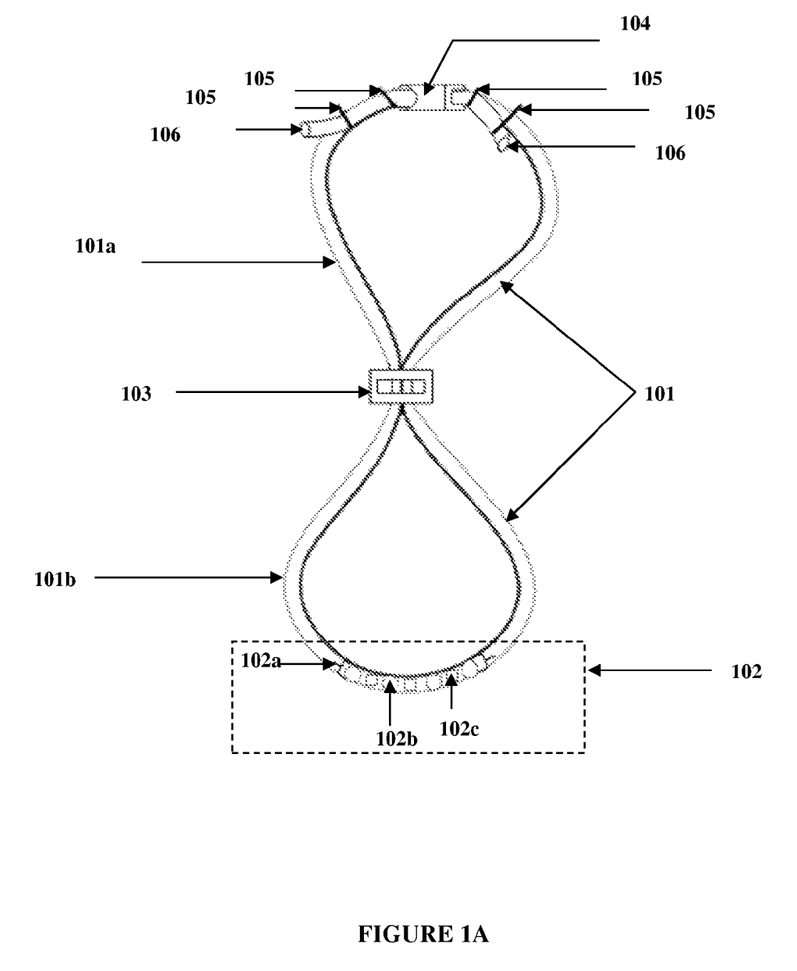
FIG. 1A exemplarily illustrates a therapeutic device for achieving and sustaining erection of a penile organ.

FIG. 1A exemplarily illustrates a therapeutic device for achieving and sustaining erection of a penile organ 201. The therapeutic device is used to treat erectile dysfunction (ED) in men. Further, the therapeutic device may be used for early penile rehabilitation. The early penile rehabilitation prevents ED in men who have undergone radical prostatectomy. The probability of contracting ED increases in men after the radical prostatectomy. Hence, early penile rehabilitation is required to maintain a healthy penile tissue after the radical prostatectomy.

Figure 6:
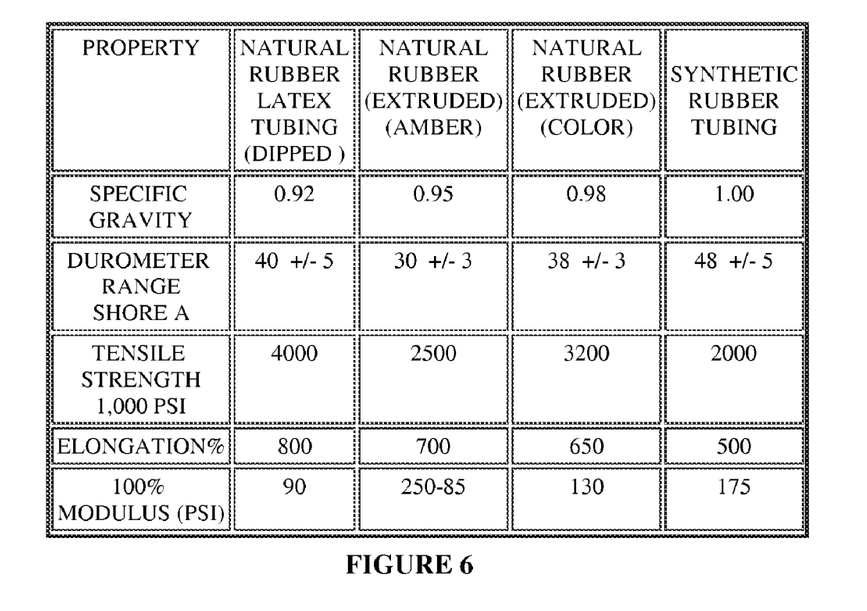
FIG. 6 illustrates a table with properties of an elastic tube used in the therapeutic device.

The therapeutic device comprises a flexible belt 101 worn by a user for producing an external pressure on one or more regions of the penile organ 201. The regions typically include top and sides of the penile organ 201. The flexible belt 101 may be a hollow elastic tube or a cord. The properties of an elastic tube used in the therapeutic device are depicted in the table illustrated in FIG. 6. The flexible belt 101 may be manufactured from natural rubber or synthetic rubber. The natural rubber latex tube or cord is produced using a continuous dipped manufacturing process. Using the continuous dipped manufacturing process, an elastic tube with undetectable levels of protein, typically, less than 50 micro grams per gram (µg/g) may be manufactured. The flexible belt 101 may be of multiple shapes, sizes, colors, or a combination thereof. Exemplarily, the flexible belt 101 may have a thickness of 0.062 inches and an internal diameter of 0.250 inches with an overall length of 5 to 6 feet.

The flexible belt 101 may be manufactured from dry natural rubber using an extrusion process. The extrusion process is a manufacturing process used to produce objects with a fixed cross-sectional profile. By the extrusion process, the elastic tube with undetectable levels of protein, typically less than 50 µg/g may be manufactured. Further, the flexible belt 101 manufactured using the synthetic rubber is latex free and may be used by latex-sensitive users of the therapeutic device.

Figure 2A:
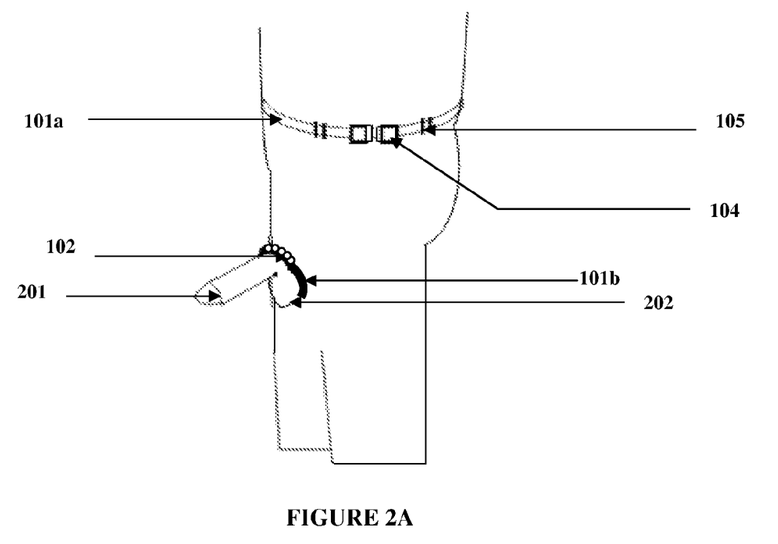
FIG. 2A exemplarily illustrates a side view of a user with the therapeutic device.

The flexible belt 101 includes a waist section 101a and a loop section 101b. The user wears the waist section 101a around the waist. The user adjusts the external pressure on the penile organ 201 using the waist section 101a. The waist section 101a comprises multiple rings 105 for adjusting length of the flexible belt 101. The rings 105 are placed on ends 106 of the waist section 101a. The rings 105 may be made of rubber and used to adjust the working length of the flexible belt 101 for comfort, fit, and for the proper application of the external pressure produced on the top and the sides of the penile organ 201. The loop section 101b worn on dorsal region of the penile organ 201 produces the external pressure on the top and sides of the penile organ 201. The side view of a user with the therapeutic device is exemplarily illustrated in FIG. 2A.

Figure 2B:
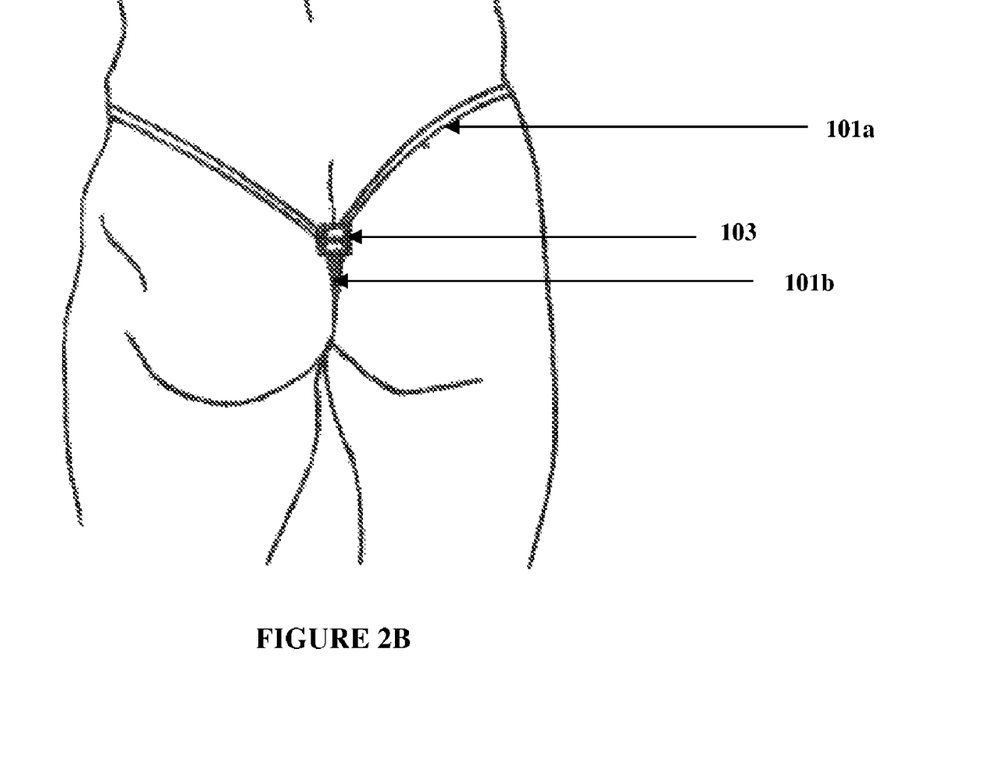
FIG. 2B exemplarily illustrates a rear view of a user with the therapeutic device.

The external pressure on the penile organ 201 restricts blood flow in veins carrying blood out of the penile organ 201. Further, the external pressure on the penile organ 201 permits the blood flow in arteries carrying blood into the penile organ 201. The user passes the loop section 101b over either side of the penile organ 201 and continues around either side of scrotum 202. The user then passes the loop section 101b under the body and up the opening between the buttocks through an adjustable buckle 103 at the top of the buttocks. The loop section 101b joins the waist section 101a along posterior end of the user. The ends 106 of the waist section 101a are joined with a buckle clamp 104. The adjustable buckle 103 is a fastener with length adjusting features and may be in the shape of an "H". Many variations of the fastener such as double or single buckles or rings 105 may be used. The buckle clamp 104 is a two sided fastener that allows the ends 106 of the flexible belt 101 to pass through either side of the fastener. The rear view of a user with the therapeutic device is exemplarily illustrated in FIG. 2B.

A magnetic unit 102 placed inside the loop section 101b produces a magnetic field. The magnetic field increases level of oxygen to augment the blood flow in the penile organ 201. The magnetic unit 102 includes one of disc shaped neodymium magnets 102c, magnetic hematite stones 102b, or a combination thereof. Exemplarily, the magnetic unit 102 may comprise three neodymium magnets 102c and four magnetic hematite stones 102b. The magnetic hematite stones 102b may be 6 millimeters (mm) in size. The neodymium magnets 102c improve the magnetic field strength required for augmenting the blood flow in the penile organ 201. Exemplarily, a neodymium magnet may have the following dimensions.

Dimensions: ⅜ inches (") diameter×⅛" thick
Dimensional tolerance: ±0.002"×±0.002"
Material grade: N42
Plating/Coating: Ni—Cu—Ni (Nickel)
Magnetization Direction Axial (Poles on Flat Ends)
Weight: 0.0599 ounce (oz)
Pull Force: 8.89 pound-force (lbs)
Surface Field: 3240 Gauss
$Br_{max}$: 13,200 Gauss
$BH_{max}$: 42 megagauss-oersted (MGOe)

The dimensions of the magnet indicate the physical size of the magnet including plating or coating. The dimensional tolerance is an allowance given as a permissible range in the nominal dimensions of a finished magnet. The purpose of the tolerance is to specify the allowed leeway for imperfections in manufacturing the neodymium magnets 102c. The neodymium magnets 102c are graded by the magnetic material they are made from. Generally, higher grades of a magnet indicate a stronger magnet. The grade of the neodymium magnets 102c range from, for example, N27 to N52. The theoretical limit for neodymium magnets 102c is grade N64. An N42 graded neodymium magnet may provide the optimal balance between strength and cost. The neodymium magnets 102c are plated or coated in order to protect the magnet material from corrosion. The neodymium magnets 102c are mostly composed of neodymium, iron, and boron.

Figure 1B:
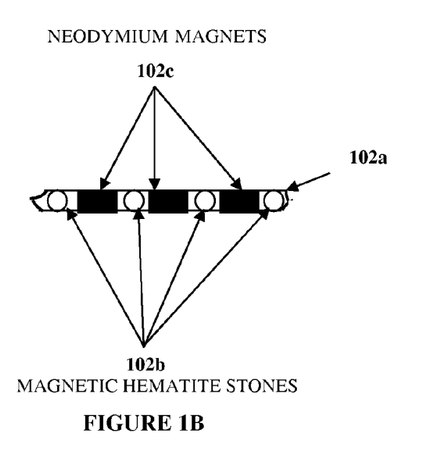
FIG. 1B exemplarily illustrates a side view of the magnetic unit of the therapeutic device.
Figure 1C:
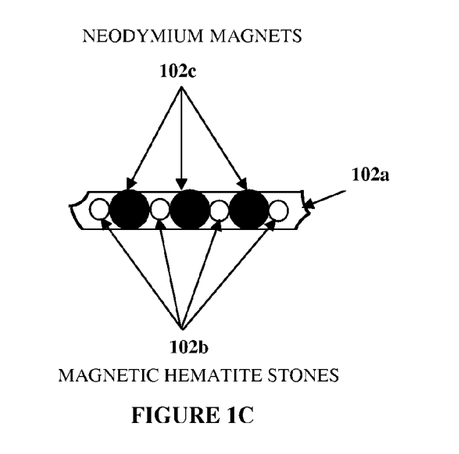
FIG. 1C exemplarily illustrates a top view of the magnetic unit of the therapeutic device.
Figure 1D:
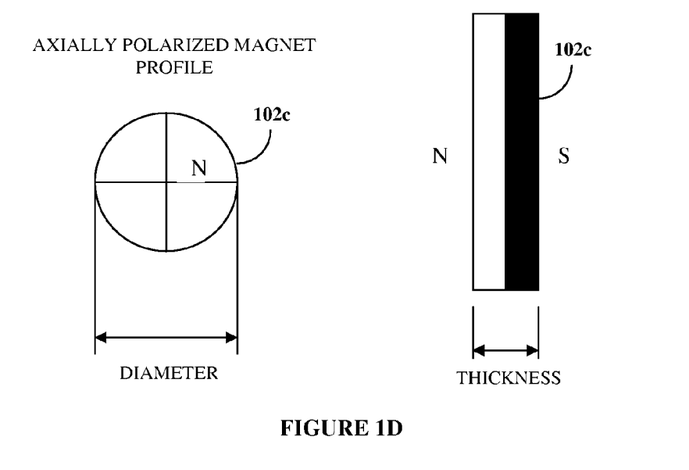
FIG. 1D exemplarily illustrates a profile of an axially polarized magnet inside the magnetic unit of the therapeutic device.

The iron in the magnet rusts if the magnet is not sealed from the environment by plating or coating. The neodymium magnets 102c may be plated in multiple layers of nickel-copper-nickel, gold, silver, black nickel, epoxy, plastic, or rubber. Exemplarily, the neodymium magnets 102c may be axially magnetized. A profile of an axially polarized magnet inside the magnetic unit 102 of the therapeutic device is illustrated in FIG. 1D. The magnetization weight indicates the weight of a single magnet. The pull force is the force required to pull a magnet free from a flat steel plate using a force perpendicular to the surface of the magnet. The surface field is the magnetic field strength at the surface of the magnet as measured by a Gauss meter. $Br_{max}$ is the residual flux density. The residual flux density is the magnetic induction remaining in a saturated magnetic material after the magnetizing field has been removed. $BH_{max}$ is the magnetic field strength at the point of maximum energy product of a magnetic material. The magnetic field strength of a completely saturated magnetic material is measured in MGOe. Furthermore, the neodymium magnets 102c may be of multiple dimensions, shapes, material, plating/coating, weight, pull force, surface field, the $Br_{max}$, or the $BH_{max}$.

The magnetic unit 102 is placed at the center of the flexible belt 101. If the flexible belt 101 is a hollow elastic tube, the magnetic unit 102 is inserted into the flexible belt 101. Further, if the flexible belt 101 is a cord, the magnetic unit 102 may be affixed to the flexible belt 101. The flexible belt 101 accommodates the magnetic unit 102 inside the hollow elastic tube. The neodymium magnets 102c, magnetic hematite stones 102b or the combination thereof, are held together by a unit holder 102a. The side view and top view of the magnetic unit 102 of the therapeutic device is exemplarily illustrated in FIGS. 1B-1C respectively.

The unit holder 102a is a heat shrinking tube and may be of one or more shapes. Further, the unit holder 102a holds one of the set of neodymium magnets 102c, the magnetic hematite stones 102b, or the combination thereof, in a predetermined configuration and polarized position. The unit holder 102a may be manufactured from a combination of materials. Exemplarily, the unit holder 102a may be of the following specifications, size 7 mm; length: 2.5 inches; temperature rating 105° C. and shrink rate 2:1.

Figure 5:
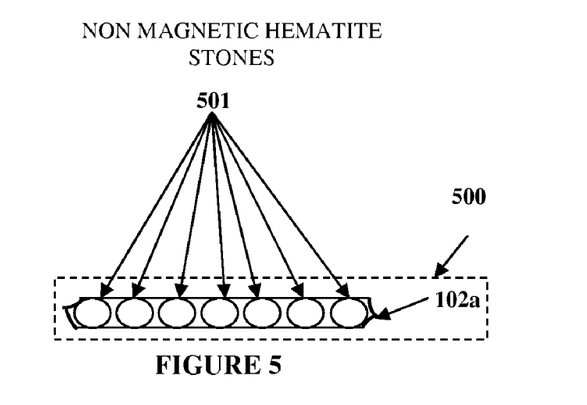
FIG. 5 exemplarily illustrates side view of a non magnetic unit of the therapeutic device.

In an embodiment of the therapeutic device disclosed herein, users with implanted pacemakers or any other electronic implanted devices are provided with a non magnetic unit. The non magnetic unit 500 includes non magnetic hematite stones 501. The non magnetic hematite stones 501 are held together by the unit holder 102a. The flexible belt 101 accommodates the non magnetic unit 500 inside the elastic tube. The non magnetic unit 500 is placed in the center of the flexible belt 101. The side view of the non magnetic unit 500 of the therapeutic device is illustrated in FIG. 5. The hematite stones, 102b or 501, are typically in the shape of rounded beads, but may be in other shapes and sizes. Exemplarily, the non magnetic unit 500 may comprise seven non magnetic hematite stones 501. The non magnetic round hematite stones 501 may be also of 6 mm in size.

The erection of the penile organ 201 requires more blood flowing into the penile organ 201 than flowing out of the penile organ 201. Sustaining the erection requires maintaining the blood flow in the penile organ 201. A polarized magnetic field produced by the neodymium magnets 102c and the magnetic hematite stones 102b penetrates tissues and arteries of the penile organ 201. With normal stimulation of the penile organ, for example, during foreplay, an initially flaccid penile organ 201 receives increased flow of oxygenated blood and achieves erection instantly. At the same time, the therapeutic device applies firm yet comfortable external pressure on the top and the sides of the penile organ 201. Since the veins of the penile organ 201 are located near the skin surface, squeezing the veins on the top and the sides prevent blood from flowing out of the penile organ 201. The squeezing of the veins traps the blood in the penile organ 201. More pressure applied to the top and the sides of the penile organ 201 corresponds to a harder erection, since less blood goes out with the same amount of the blood coming constantly into the penile organ 201.

The magnetic field applied on the penile region and the adjustment of the external pressure enables the user to achieve and sustain the erection of the penile organ 201. By using the therapeutic device, the user achieves faster and harder erection, and sustains erection even after ejaculation as long as the external pressure is applied on the penile organ 201. Further, a user with premature ejaculation may sustain erection even after the ejaculation. Moreover, the therapeutic device is reusable and economical.

Figure 3:
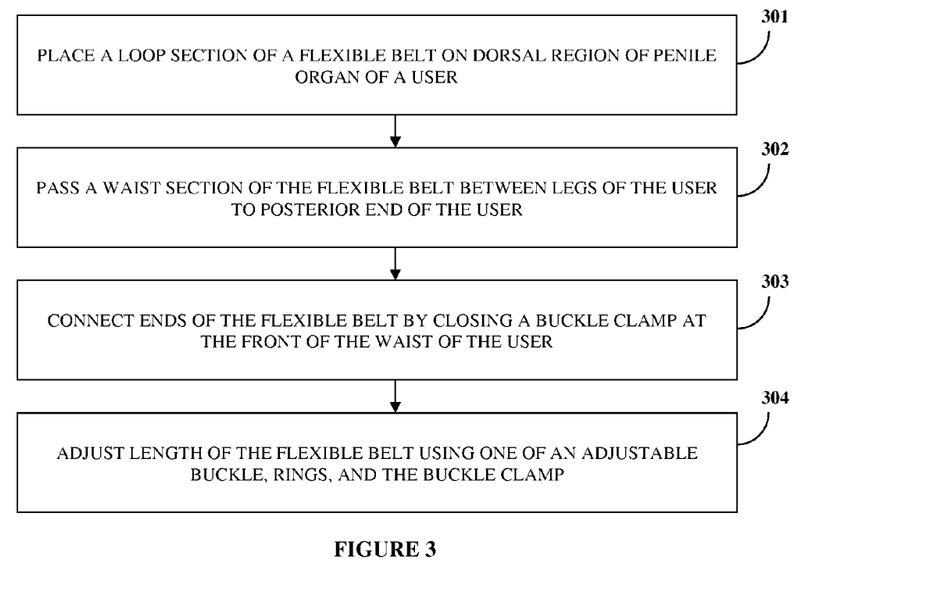
FIG. 3 illustrates a method of achieving and sustaining erection of a penile organ.

FIG. 3 illustrates a method of achieving and sustaining erection of a penile organ 201. A user places 301 a loop section 101b of a flexible belt 101 on the dorsal region of the penile organ 201 of the user. The loop section 101b includes a magnetic unit 102 to produce a magnetic field to augment blood flow in the penile organ 201. The user places the loop section 101b with north side of the magnetic unit 102 facing towards the penile organ 201. The user passes 302 a waist section 101a of the flexible belt 101 between the legs to the posterior end of the user. A buckle clamp 104 attached to ends 106 of the waist section 101a is kept in an open position. Further, the user connects 303 the ends 106 of the waist section 101a by closing the buckle clamp 104 in front of the waist of the user. The user then adjusts 304 length of the flexible belt 101 using one of an adjustable buckle 103 or rings 105, along with the buckle clamp 104. The adjustment of the length of the flexible belt 101 provides an external pressure on the dorsal region of the penile organ 201. The external pressure may be applied on the top and sides of the penile organ 201.

The user may move the adjustable buckle 103 towards the loop section 101b in order to reduce the length of the loop section 101b and at the same time to increase the length of the waist section 101a. By moving the adjustable buckle 103 towards the loop section 101b, the user may reduce the applied pressure on the penile organ 201. Further, the user may adjust the length using the rings 105 along with the buckle clamp 104. By pulling the ends 106 of the flexible belt 101 through the buckle clamp 104, the user may reduce the length of the waist section 101a. By adjusting the length of the loop section 101b and the waist section 101a, users with different waist sizes may sustain the erection. Exemplarily, a set of two rings 105 maintain a predefined length of the therapeutic device after the adjustment of the flexible belt 101. The magnetic field and the adjustment of the flexible belt 101 enable the user to sustain the erection of the penile organ 201.

Figure 4:
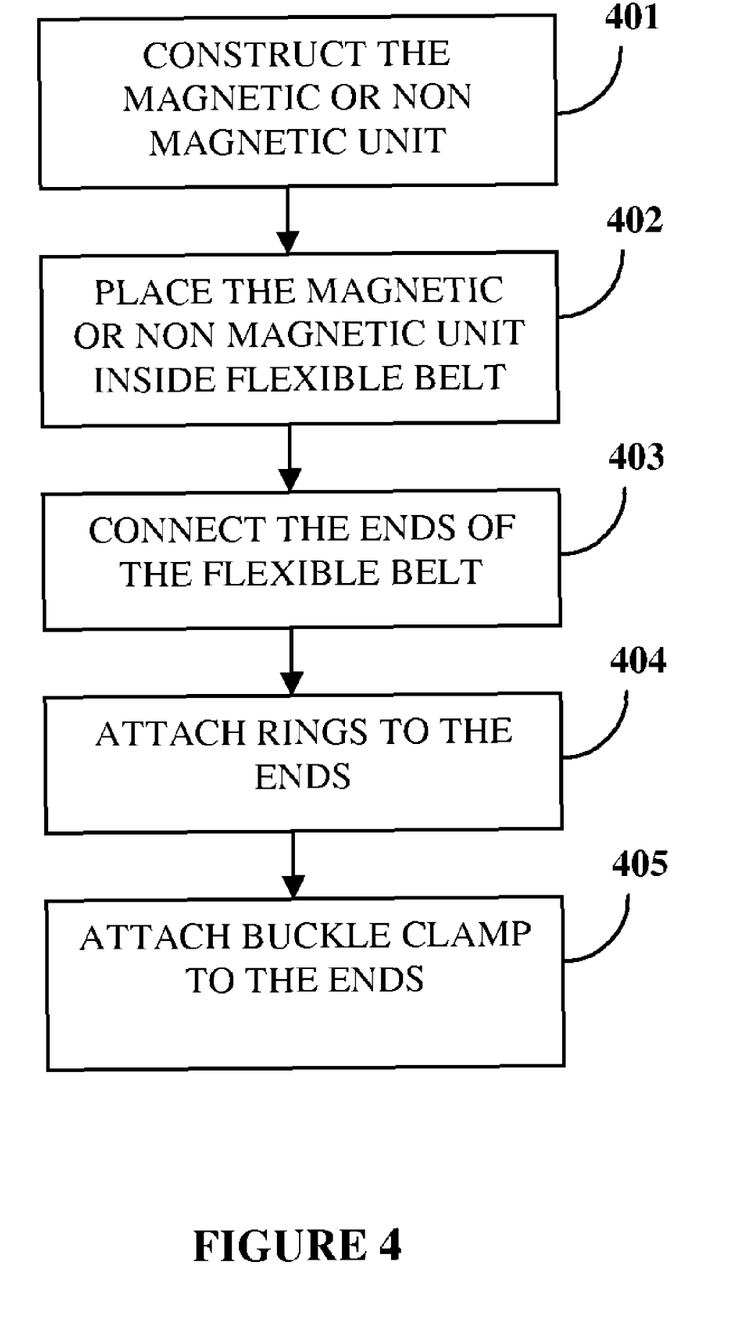
FIG. 4 exemplarily illustrates a method of manufacturing the therapeutic device.

FIG. 4 exemplarily illustrates a method of manufacturing the therapeutic device. The construction 401 of the magnetic unit 102 or the non magnetic unit 500 includes placing three neodymium magnets 102c separated by magnetic hematite stones 102b in a heat-shrinking tube. The heat-shrinking tube provides an enclosure for the neodymium magnets 102c and the magnetic hematite stones 102b. The magnetic unit 102 or the non magnetic unit 500 is constructed in the shape of a semi circle by placing the magnetic unit 102 or the non magnetic unit 500 on a metal curve and applying heat. The heat shrinks the unit holder 102a and takes the shape of a semi circle. The neodymium magnets 102c face their north side towards the internal part of the metal curve. The magnetic unit 102 or the non magnetic unit 500 is then placed 402 inside the flexible belt 101.

The magnetic unit 102 or the non magnetic unit 500 is placed in the middle of the flexible belt 101. The adjustable buckle 103 is in the shape of an "H" and is used to connect the loop section 101b with the waist section 101a. The loop section 101b is placed with the north side of the magnetic unit 102 facing towards the penile organ 201. Length adjusting rings 105 are attached 404 to the ends 106 of the flexible belt 101. Further, a male connector end and a female connector end of a buckle clamp 104 is attached 405 to the ends 106 of the flexible belt 101 to make a second loop or the waist section 101a. The therapeutic device may be manufactured in multiple shapes, for example, as the shape of the numerical "8".

The aforementioned process flow exemplarily illustrates the manufacturing process of the therapeutic device. The magnetic unit 102 or non magnetic unit 500 may be placed inside the flexible belt 101 by air under pressure. The magnetic unit 102 or non magnetic unit 500 may be melted in the cord during production process of the cord. Exemplarily, the flexible belt 101 may have one of the following dimensions:

3/16" ID×1/16" Wall (0.187" ID×0.062" Wall)
3/16" ID×3/32" Wall (0.187" ID×0.093" Wall)
1/4" ID×1/16" Wall (0.250" ID×0.062" Wall)
1/4" ID×3/32" Wall (0.250" ID×0.093" Wall)
"ID" indicates internal diameter of the flexible belt 101. The wall means thickness of the wall of the flexible belt 101.

The foregoing examples have been provided merely for the purpose of explanation and are in no way to be construed as limiting of the present apparatus disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A therapeutic device for achieving and sustaining erection of a penile organ, comprising:
    a flexible belt adapted to be worn by a user comprising:
        a waist section adapted to be worn around waist of said user, wherein said waist section comprises a combination of a buckle clamp and a plurality of rings, wherein said buckle clamp is a two sided fastener that allows two sides of the flexible belt to pass through either side of the fastener, and wherein said rings are placed on two sides of said waist section;
        a loop section adapted to be worn on dorsal region of the penile organ of said user; and
        an adjustable buckle, wherein said adjustable buckle is generally adapted to connect the loop section and the waist section, wherein the length of the flexible belt is adjusted using one of said combination of said adjustable buckle and the rings, and the buckle clamp, and wherein said adjustment of said length of the flexible belt produces an external pressure on said penile organ of said user;
    a magnetic unit placed inside said loop section for producing a magnetic field, wherein said magnetic field increases level of oxygen to augment blood flow in the penile organ;
    whereby the magnetic field and said adjustment of the external pressure enable the user to achieve and sustain said erection of the penile organ.

2. The device of claim 1, wherein the flexible belt is one of an elastic tube or a cord.

3. The device of claim 1, wherein the external pressure produced on the penile organ restricts said blood flow in veins carrying blood out of the penile organ.

4. The device of claim 1, wherein the external pressure produced on the penile organ permits said blood flow in arteries carrying blood into the penile organ.

5. The device of claim 1, wherein the loop section joins said waist section along posterior end of the user, wherein the waist section comprises a buckle clamp to connect ends of the waist section.

6. The device of claim 1, wherein said magnetic unit comprises one or more of magnetized neodymium disc magnets and magnetic hematite stones, further wherein the magnetic unit is placed at center of the flexible belt.

7. The device of claim 1, further comprising a non magnetic unit placed at center of the flexible belt, wherein said non magnetic unit comprises one or more non magnetic hematite stones.

8. A method of achieving and sustaining erection of a penile organ, comprising:
    providing a flexible belt adapted to be worn by a user, comprising:
        a waist section adapted to be worn around waist of said user, wherein said waist section comprises a combination of a buckle clamp and a plurality of rings, wherein said buckle clamp is a two sided fastener that allows two sides of the flexible belt to pass through either side of the fastener, and wherein said rings are placed on two sides of said waist section;
        a loop section adapted to be worn on dorsal region of the penile organ of said user; and
        an adjustable buckle, wherein said adjustable buckle is generally adapted to connect the loop section and the waist section
    placing said loop section of said flexible belt on said dorsal region of penile organ of said user, wherein said loop section comprises a magnetic unit for producing a magnetic field to augment blood flow in the penile organ;
    passing said waist section of said flexible belt between legs of said user to posterior end of the user, wherein said buckle clamp attached to ends of said waist section is kept in an open position;
    connecting said ends of the waist section by closing said buckle clamp in front of waist of the user; and
    adjusting the length of the flexible belt using one of said combination of said adjustable buckle and said rings, and the buckle clamp, wherein said adjustment of said length of the flexible belt produces an external pressure on said dorsal region of the penile organ.

9. The method of claim 8, wherein the loop section is placed with north side of said magnetic unit facing towards the penile organ.

10. A therapeutic device for achieving and sustaining erection of a penile organ, comprising:
   a flexible belt adapted to be worn by a user comprising:
      a waist section adapted to be worn around waist of said user, wherein said waist section comprises a combination of a buckle clamp and a plurality of rings, wherein said buckle clamp is a two sided fastener that allows two sides of the flexible belt to pass through either side of the fastener, and wherein said rings are placed on two sides of said waist section;
      a loop section adapted to be worn on dorsal region of the penile organ of said user; and
      an adjustable buckle, wherein said adjustable buckle is generally adapted to connect the loop section and the waist section;
   whereby said adjustment of said flexible belt using one of said combination of the adjustable buckle and the plurality of rings, and the buckle clamp, produces an external pressure on said penile organ to enable the user to achieve and sustain erection of the penile organ.

* * * * *